United States Patent [19]

Seely

[11] 4,219,643

[45] Aug. 26, 1980

[54] FORTIMICIN AN
[75] Inventor: John H. Seely, Lake Forest, Ill.
[73] Assignee: Abbott Laboratories, North Chicago, Ill.
[21] Appl. No.: 25,250
[22] Filed: Mar. 29, 1979
[51] Int. Cl.$^2$ ............... A61K 31/71; C07H 15/22
[52] U.S. Cl. ............... 536/17 R; 424/180; 424/181; 536/18; 435/80
[58] Field of Search ............... 536/17 R
[56] References Cited

U.S. PATENT DOCUMENTS

| 3,878,193 | 4/1975 | Reimann | 536/17 |
| 3,963,695 | 6/1976 | Cooper et al. | 536/17 |
| 4,091,032 | 5/1978 | Tadanier et al. | 536/17 |
| 4,124,756 | 11/1978 | Martin et al. | 536/17 |

Primary Examiner—Johnnie R. Brown
Attorney, Agent, or Firm—Robert L. Niblack; Gildo E. Fato; Joyce R. Niblack

[57] ABSTRACT

Fortimicin AN is coproduced with fortimicin A, fortimicin B and a number of other minor factors in the fermentation of *Micromonospora olivoasterospora* ATCC Nos. 21819, 31009 or 31010. Structurally, fortimicin AN is 1-N-glycyl-3-O-demethylfortimicin B. The compound is useful as an intermediate for 3-O-demethylfortimicin B which is readily obtained by hydrolysis of fortimicin AN in base.

1 Claim, No Drawings

FORTIMICIN AN

BACKGROUND OF THE INVENTION

The aminoglycoside antibiotics are a valuable therapeutic class of antibiotics which include the kanamycins, gentamicins, streptomycins, sagamicins, and the more recently discovered fortimicins. While the naturally produced parent antibiotics are generally, in themselves, valuable antibiotics, chemical modifications have been found to improve the activity, either intrinsic activity or activity against resistant strains or against one or more strains the parent antibiotic is not effective against. Thus, chemical modification has provided both alternative therapeutic agents as well as those which are held in reserve because of the resistance problem. And, because of the development of aminoglycoside-resistant strains and inactivation of the parent antibiotics by R-mediated factors which can develop, the search for new therapeutic entities continues.

Further, some of the naturally produced, parent antibiotics, such as fortimicin B and fortimicin E, are primarily useful as intermediates in preparing derivatives which have more potent antibacterial properties than their weakly active parent antibiotics. The present invention provides one such fortimicin, fortimicin AN.

The fortimicin of this invention is co-produced in the fermentation of *Micromonospora olivoasterospora* ATCC No. 21819, 31009 or 31010 according to the method of Nara et al. U.S. Pat. Nos. 3,931,400 and 3,976,768 which disclose the production of fortimicin A and fortimicin B.

Fortimicin AN is a minor factor which is co-produced with fortimicin A, fortimicin B and a number of other minor factors which are disclosed and claimed in commonly assigned, copending patent applications Ser. Nos. 025,241; 025,243; 025,247; 025,251; and 025,252. filed on even date herewith and with the minor factors isofortimicin and fortimicin E which are disclosed and claimed in commonly assigned, co-pending application Ser. Nos. 863,015 and 863,016, both filed Dec. 21, 1977.

SUMMARY OF THE INVENTION

The present invention provides an new fortimicin, fortimicin AN. Fortimicin AN can also be named as 1-N-glycyl-3-O-demethylfortimicin B. The compound is useful as an intermediate in preparing 3-O-demethylfortimicin B which is disclosed and claimed in U.S. Pat. No. 4,124,756.

DETAILED DESCRIPTION OF PREFERRED EMBODIMENTS

The compound of this invention, fortimicin AN, is represented by the formula:

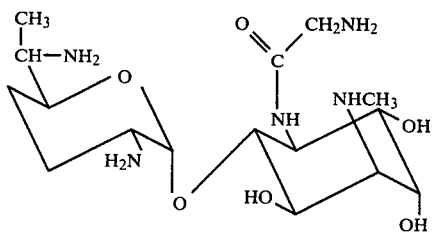

Fortimicin AN can be prepared by the fermentation of Micromonospora olivoasterospora ATCC No. 21819, 31009 or 31010 according to the methods described by Nara et al. in U.S. Pat. Nos. 3,931,400 and 3,976,768 for the fermentation of fortimicin A and fortimicin B and as set forth in detail in Examples 1-4.

Fortimicin AN is useful as an intermediate in the synthesis of 3-O-demethylfortimicin B which is disclosed and claimed in U.S. Pat. No. 4,124,756. Generally speaking, 3-O-demethylfortimicin B can be obtained directly from fortimicin AN by hydrolysis with a suitable base, such as barium hydroxide which removes the 1-N-glycyl group and affords the desired product.

The following examples further illustrate the present invention.

EXAMPLE 1

Preparation of Fermentation Broth

6000 Liters of a fermentation broth having the following composition and pH 7 before sterilization is prepared:

| Ingredient | Weight Percent |
|---|---|
| Starch | 4.00 |
| Soybean meal | 2.00 |
| Cornsteep liquor | 0.05 |
| $K_2HPO_4$ | 0.05 |
| $MgSO_4 \cdot 7H_2O$ | 0.05 |
| KCl | 0.03 |
| $CaCO_3$ | 0.10 |
| Water | to 100 |

EXAMPLE 2

Preparation of Inoculum

*Micromonaspora olivoasterospora* ATCC 21819 is used as a seed strain and is intitally cultured in a first see medium containing 2% glucose, 0.5% peptone, 0.5% yeast extract and 0.1% calcium carbonate (pH 7.2 before sterilization) by inoculating one loopful of the seed strain into 10 ml of the seed medium in a 50 ml large test tube. Culturing is carried out at 30° C. for 5 days with shaking. Ten ml of the seed culture broth is then inoculated into 30 ml of a second seed medium in a 250 ml Erlenmeyer flask. The composition of the second seed medium is the same as that of the first seed medium. The second seed culturing is carried out at 30° C. for two days with shaking.

Then 30 ml of the second seed culture broth is inoculated into 300 ml of a third seed medium in a two liter Erlenmeyer flask provided with baffles. The composition of the third seed medium is the same as that of the first seed medium and the third seed culturing is carried out at 30° C. for 2 days with shaking. Thereafter, 1.5 liters of the third seed culture broth (corresponding to the contents of five flasks) is inoculated into 15 liters of a fourth seed medium in a 30 liter glass jar fermenter. The composition of the fourth seed medium is the same as that of the first seed medium. Culturing in the jar fermenter is carried out at 30° C. for two days with aeration (15 liters/min.) and stirring (350 r.p.m).

EXAMPLE 3

Production of Fortimicin AN

Fifteen liters of the fourth seed cultuer broth of Example 2 is inoculated into 150 liters of a main fermentation medium in a 300 liter stainless steel fermenter. The main fermentation medium comprises: 4% starch, 2% soybean meal, 1% corn steep liquor, 0.05% $K_2HPO_4$, 0.05% MgSO$_4$·7 H$_2$O), 0.3% KCl and 0.1% CaCO$_3$ and water (pH 7.0 before sterilization). Culturing in the fermenter is carried out at 30° C. for 4 days with aeration (80 liters/min. and stirring (150 r.p.m).

EXAMPLE 4

Isolation of Fortimicin AN

To 5000 liters of the fermentation broth, prepared as described above, is added 102 liters of a weakly acidic carboxylic(polymethacrylate) type cation exchange resin in the ammonia form, e.g. Amberlite IRC-50 sold by the Rohm and Haas Company. The mixture is agitated for two hours, during which time the mixture is maintained at pH 6.6 by the addition of sulfuric acid. The ion exchange resin is separated from the broth by centrifugation and then added to a column and backwashed with deionized water until free of extraneous solids. The column is washed with water, then eluted downflow with 1 N-ammonium hydroxide. Elutes of pH 9.6 to about 11.3 are collected and concentrated under reduced pressure until excess ammonia is removed. The solution is adjusted to pH 2.0 with hydrochloric acid and treated with 5% (w/v) activated carbon such as Pittsburgh RB carbon sold by Calgon Corporation. The solution is then filtered through a diatomaceous earth mat and the filtrant concentrated under reduced pressure to give a mixture of crude fortimicins. (265 g.).

A portion of the crude fortimicins (265 g.), prepared as described above, is dissolved in 8 liters of water and the solution adjusted to pH 9 with ammonium hydroxide. To facilitate isolation of fortimicin AN, fortimicin A is hydrolyzed to fortimicin B by heating the solution to 70° C. for 20 hours, maintaining a pH 9 by the controlled addition of ammonium hydroxide. After filtration through a mat of diatomaceous earth, the reaction mixture is concentrated under reduced pressure to approximately 3.6 liters. A portion of this material (1.8 liters) is diluted to 15 liters with water and adjusted to pH 6.8 with hydrochloric acid. The solution is charged on a column containing 7 liters of a weakly acidic, carboxylic(polymethacrylate) type, cation exchange resin in the ammonia form, e.g. Amerlite JRC-50. After washing with water, the column is eluted with 20 liters of 0.1 N ammonium hydroxide. One liter fractions are collected and examined by thin layer chromatography using Whatman No. 1 filter paper. Development is carried out at room temperature for 10 to 15 hours using a solvent system consisting of the lower phase of a mixture of methanol-chloroform-concentrated ammonium hydroxide[1:1:1(v/v/v)].

Fractions 1–2: Unidentified minor components
Fractions 3–4: Isofortimicin
Fraction 5: Isofortimicin and fortimicin B
Fractions 6–10: Fortimicin B
Fractions 11–20: Unidentified minor components A portion of the crude fortimicins is chromatographed on a column of Dowex CG-50 resin eluted with 0.3 M ammonium hydroxide. Initial and final fractions are discarded. The median fractions are combined, adjusted to pH 2.0 with sulfuric acid and treated with carbon. The mixture is filtered and the pH of the filtrate is adjusted to pH 6.0 with Dowex CG-50 WGR resin in the ammonia form and the resin removed. The solution is concentrated and rechromatographed over a column of Dowex CG-50 resin resin eluted with 0.125 N ammonium hydroxide. Initial fractions are combined and adjusted to pH 6 with sulfuric acid. Amberlite IR-124 resin in the ammonia form (3 liters) is added and after 30 minutes filtered off and washed with water. The combined filtrates and washings are treated with 300 g of Pittsburg RB carbon sold by Calgon Corporation. The mixture is filtered. The precipitate is washed with water and the combined filtrate and washings are treated with 4 liters of Dowex WGR resin in the ammonia form and the resin removed. The filtrate (at pH 6) is concentrated to a residue.

A portion of the residue is chromatographed on a column of Bio Rex 70 resin in the ammonia form (2.5 cm diam × 40 cm) washed well with water and eluted with a stepwise gradient of 0.3 N, 0.5 N and 1.0 N ammonium hydroxide. Later fractions from the column are combined and concentrated to give 1.4 g of solid material. A portion of this (1 g) is chromatographed on a column of Sephadex G-15 resin in 0.01 N acetic acid. Initial fractions yield fortimicin AN (459 mg). Proton magnetic resonance spectrum measured in deuterium oxide with tetramethylsilane as external reference: δ1.46 (3H) doublet 7'-CH$_3$; δ2.82 (3H) singlet NCH$_3$; δ3.80 (2H) singlet gly-CH$_2$; δ5.76 (1H) doublet C$_1$'-H.

EXAMPLE 5

3-O-Demethylfortimicin B

A solution of one gram of fortimicin AN in 100 ml of 2 N aqueous barium hydroxide is heated under reflux for 22 hours, allowed to cool and saturated with carbon dioxide. The mixture is filtered through a mat of celite and the filtrate is concentrated to a residue of crude product. This is purified by chromatography on a column of silica gel developed with the lower phase of a mixture of equal volumes of chloroform, methanol and concentrated ammonium hyroxide. Fractions containing the major component are pooled and concentrated to yield 3-O-demthylfortimcin B(700 mg).

We claim:

1. Fortimicin AN represented by the formula:

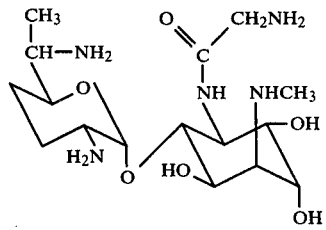

and the pharmaceutically acceptable salts thereof.

* * * * *